US010182710B2

(12) United States Patent
Sezan et al.

(10) Patent No.: US 10,182,710 B2
(45) Date of Patent: Jan. 22, 2019

(54) WEARABLE DUAL-EAR MOBILE OTOSCOPE

(71) Applicant: QUALCOMM Incorporated, San Diego, CA (US)

(72) Inventors: Muhammed Ibrahim Sezan, Los Gatos, CA (US); Eugene Dantsker, San Diego, CA (US); Kenneth Kaskoun, La Jolla, CA (US); Brian David Niznik, San Diego, CA (US); Christopher Talbot, San Diego, CA (US); Ilene Klein, Del Mar, CA (US)

(73) Assignee: QUALCOMM Incorporated, San Diego, CA (US)

( * ) Notice: Subject to any disclaimer, the term of this patent is extended or adjusted under 35 U.S.C. 154(b) by 545 days.

(21) Appl. No.: 14/807,700

(22) Filed: Jul. 23, 2015

(65) Prior Publication Data

US 2017/0020382 A1   Jan. 26, 2017

(51) Int. Cl.
A61B 1/267 (2006.01)
A61B 1/227 (2006.01)
A61B 1/00 (2006.01)
A61B 1/05 (2006.01)
A61B 1/07 (2006.01)
(Continued)

(52) U.S. Cl.
CPC .......... *A61B 1/227* (2013.01); *A61B 1/00009* (2013.01); *A61B 1/00016* (2013.01); *A61B 1/05* (2013.01); *A61B 1/07* (2013.01); *A61B 5/0002* (2013.01); *A61B 5/01* (2013.01); *A61B 5/6803* (2013.01); *A61B 5/6817* (2013.01); *A61B 5/746* (2013.01); *A61B 5/7465* (2013.01)

(58) Field of Classification Search
CPC combination set(s) only.
See application file for complete search history.

(56) References Cited

U.S. PATENT DOCUMENTS 7,901,351 B2   3/2011   Prescott
8,469,882 B2   6/2013   Andreassen et al.
(Continued)

FOREIGN PATENT DOCUMENTS

WO   2014092932   6/2014

OTHER PUBLICATIONS

International Search Report and Written Opinion—PCT/US2016/037646—ISA/EPO—dated Apr. 4, 2017.
(Continued)

*Primary Examiner* — Sameh Boles
(74) *Attorney, Agent, or Firm* — Weaver Austin Villeneuve & Sampson LLP—QUAL

(57) ABSTRACT

A wearable otoscope may be capable of wireless or wired communication with a second device, such as a smart phone. Some dual-ear otoscope implementations may be provided in a headphone-like configuration, which may include a headband attachable to earbuds of the dual-ear otoscope. However, some alternative implementations do not include a headband. At least a portion of the dual-ear otoscope may be a disposable component in some examples. In some implementations, functionality of the dual-ear otoscope (such as an illumination angle of light, imaging functionality, etc.) may be controlled according to commands received from the second device. Some examples may include one or more additional sensors, such as temperature sensors.

24 Claims, 11 Drawing Sheets

(51) Int. Cl.
*A61B 5/00* (2006.01)
*A61B 5/01* (2006.01)

(56) References Cited

U.S. PATENT DOCUMENTS

| | | |
|---|---|---|
| 2009/0312638 A1 | 12/2009 | Bartlett |
| 2010/0217098 A1 | 8/2010 | LeBoeuf et al. |
| 2011/0004089 A1 | 1/2011 | Chou |
| 2011/0224493 A1 | 9/2011 | Oyadiran et al. |
| 2014/0073880 A1* | 3/2014 | Boucher ................ A61B 1/227 600/301 |
| 2014/0243941 A1 | 8/2014 | Rogers et al. |
| 2015/0065803 A1 | 3/2015 | Douglas et al. |

OTHER PUBLICATIONS

Partial International Search Report—PCT/US2016/037646—ISA/EPO—dated Sep. 5, 2016.

* cited by examiner

WEARABLE DUAL-EAR MOBILE OTOSCOPE

TECHNICAL FIELD

This disclosure relates generally to mobile health devices, methods and systems.

DESCRIPTION OF THE RELATED TECHNOLOGY

Ear infections are the most common reason for pediatrician visits, accounting for approximately 30 million doctor visits per year in the United States. Some types of healthcare are now being provided in homes or pharmacy kiosks, in addition to hospitals and doctors' offices. Therefore, it would be desirable to have an otoscope that is easier to use by technicians, parents or patients in a home or a pharmacy setting.

SUMMARY

The systems, methods and devices of the disclosure each have several innovative aspects, no single one of which is solely responsible for the desirable attributes disclosed herein.

One innovative aspect of the subject matter described in this disclosure can be implemented in an apparatus that may include a first earbud, a second earbud and a light source system that includes at least one light source. The apparatus may include a light-conveying system capable of conveying light from the light source system to a user's first ear and to the user's second ear, via the first earbud and the second earbud. In some examples, the apparatus may include an image sensor system capable of forming images based, at least in part, on light reflected from the user's first ear and the user's second ear. According to some implementations, the apparatus may include a control system capable of controlling the light source system and the image sensor system.

In some implementations, the apparatus may include an interface system. According to some such implementations, the interface system may be capable of wireless communication with a second device. In some examples, the interface system may include one or more types of user interface. According to some examples, the control system may be capable of receiving instructions from the second device, via the interface system and of controlling the apparatus according to the instructions.

According to some examples, the control system may be capable of providing image data to the second device. According to some such examples, the control system may be capable of compressing the image data prior to transmitting the image data to the second device. In some implementations, the control system may be capable of encrypting the image data prior to transmitting the image data to the second device.

In some examples, the light-conveying system may include optical fibers. According to some implementations, the light-conveying system may be capable of conveying the light reflected from the user's first ear and the user's second ear to the image sensor system.

According to some examples, the apparatus may include first optical elements capable of coupling light from the light source system into the light-conveying system. The apparatus also may include second optical elements capable of directing light from the light-conveying system into the user's first ear and the user's second ear. According to some examples, the second optical elements may include micromechanical systems (MEMS) devices. According to some such implementations, the control system may be capable of controlling illumination angles of light provided by the second optical elements. In some implementations, the apparatus may include third optical elements capable of coupling light reflected from the user's first ear and the user's second ear into the light-conveying system.

In some implementations, the apparatus may include a headband attachable to the first earbud and the second earbud. The headband may be capable of holding the first earbud in a user's first ear and of holding the second earbud in the user's second ear. According to some such implementations, at least a portion of the light-conveying system may be attached to the headband.

According to some examples, the first earbud, the second earbud, or both the first and second earbuds, may include at least a portion of the image sensor system. In some implementations, at least a portion of the control system may be disposed within the first earbud, the second earbud, or both the first and the second earbud.

In some implementations, the first earbud and the second earbud may include deformable material. According to some such implementations, the deformable material may include actively deformable material. In some examples, the actively deformable material may include an electroactive polymer. In some such implementations, the control system may be capable of controlling deformation of the actively deformable material.

According to some examples, the apparatus may include a temperature sensor capable of measuring the user's body temperature. In some implementations, the apparatus may include a biometric sensor system capable of obtaining biometric information from the user. For example, the biometric sensor system may include a speaker and a microphone. According to some such examples, the control system may be capable of controlling the speaker to generate input acoustic signals while controlling the microphone to obtain output acoustic signals corresponding to the reflections of the input acoustic signals from a user's ear canal. In some such examples, the control system may be capable of determining a transfer function based, at least in part, on the input acoustic signals and the output acoustic signals. In some implementations, the biometric sensor system may include a fingerprint sensor system.

Some or all of the methods described herein may be performed by one or more devices according to instructions (e.g., software) stored on non-transitory media. Such non-transitory media may include memory devices such as those described herein, including but not limited to random access memory (RAM) devices, read-only memory (ROM) devices, etc. Accordingly, other innovative aspects of the subject matter described in this disclosure can be implemented in a non-transitory medium having software stored thereon.

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale.

DETAILED DESCRIPTION

Figure 1:
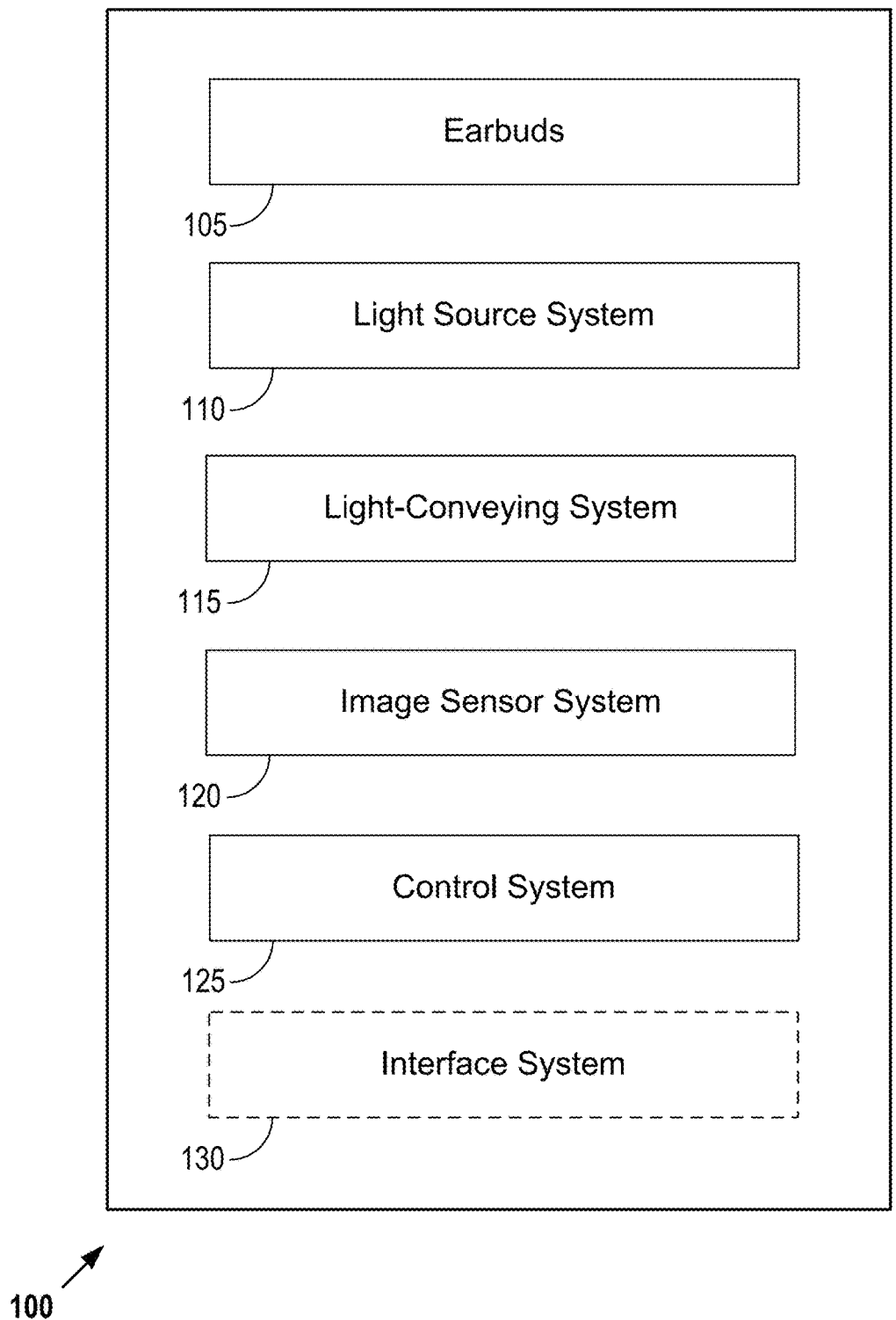
FIG. 1 is a block diagram that shows examples of components of a device in which some aspects of the present disclosure may be implemented.

The following description is directed to certain implementations for the purposes of describing the innovative aspects of this disclosure. However, a person having ordinary skill in the art will readily recognize that the teachings herein may be applied in a multitude of different ways. It is contemplated that the described implementations may be included in or associated with a variety of electronic devices such as, but not limited to: mobile telephones, multimedia Internet enabled cellular telephones, mobile television receivers, wireless devices, smartphones, Bluetooth® devices, personal data assistants (PDAs), wireless electronic mail receivers, hand-held or portable computers, netbooks, notebooks, smartbooks, tablets, global positioning system (GPS) receivers/navigators, cameras, camcorders, wrist watches, electronic reading devices (e.g., e-readers), mobile health devices, etc. The teachings herein also may be used in applications such as, but not limited to, electronic switching devices, radio frequency filters, sensors, including but not limited to biometric sensors, accelerometers, gyroscopes, motion-sensing devices, magnetometers, inertial components for consumer electronics, parts of consumer electronics products, varactors, liquid crystal devices, electrophoretic devices, etc. Thus, the teachings are not intended to be limited to the implementations depicted solely in the Figures, but instead have wide applicability as will be readily apparent to one having ordinary skill in the art.

Some implementations provide a wearable dual-ear otoscope. Some dual-ear otoscope implementations may be provided in a headphone-like configuration, which may include a headband attachable to earbuds of the dual-ear otoscope. However, some alternative implementations may not include a headband. In some examples, at least a portion of the dual-ear otoscope may be a disposable component. In some implementations, the dual-ear otoscope is capable of wireless or wired communication with a second device, such as a smart phone. Wireless implementations do not need to be physically connected with the second device. In some implementations, functionality of the dual-ear otoscope (such as an illumination angle of light, imaging functionality, etc.) may be controlled according to commands received from the second device. Some examples may include one or more additional sensors, such as temperature sensors.

Some dual-ear otoscopes disclosed herein may be capable of aligning with earbuds properly without user adjustment and/or holding the dual-ear otoscope firmly in place. Accordingly, some dual-ear otoscopes disclosed herein may be relatively easier to use than single-ear otoscopes that are intended for use by physicians. Therefore, some dual-ear otoscopes disclosed herein may be more suitable for use in the home or in a pharmacy setting. Some dual-ear implementations may allow both ears of a patient to be examined in less time than it would take for a doctor to examine both ears with a single-ear otoscope.

FIG. 1 is a block diagram that shows examples of components of a dual-ear otoscope in which some aspects of the present disclosure may be implemented. As with other implementations disclosed herein, the numbers of elements and types of elements shown in FIG. 1 are merely shown by way of example. Other implementations may have more, fewer or different elements. In the implementation shown in FIG. 1, the dual-ear otoscope system 100 includes earbuds 105, a light source system 110, a light-conveying system 115, an image sensor system 120 and a control system 125.

The earbuds 105 may include various materials, depending on the particular implementation. In some implementations, the earbuds 105 may be disposable components of the otoscope system 100. In such implementations, the ear buds 105 may be formed of relatively inexpensive components and may, for example, be intended for a single use. In some such implementations, the earbuds 105 may be configured to be manually attachable to, and detachable from, a connecting element (such as a headband) without requiring the use of any tool. For example, the earbuds 105 may be configured to snap on and off of the headband. According to some such implementations, the earbuds 105 may be separate from other components of the dual-ear otoscope 100 such as the image sensor system 120 and/or the control system 125. This may allow for disposability of the ear-buds 105 without affecting the operation of the dual-ear otoscope 100.

In some examples, the earbuds 105 may include deformable material, such as silicone, memory foam, rubber, etc. According to some implementations, the deformable material may include actively deformable material, such as an electroactive polymer. According to some such implementations, the control system 125 may be capable of controlling deformation of the actively deformable material. For example, the control system 125 may be capable of controlling deformation of the actively deformable material in order to optimally position a portion of the light-conveying system 115 that is attached to an earbud 105. In some examples, the control system 125 may be capable of controlling deformation of the actively deformable material in order to position a portion of a light-coupling system, such as a lens, that is attached to an earbud 105. The light-coupling system may, for example, be a component of the light-conveying system 115. Some examples are described below.

The light source system 110 may include at least one light source. In some examples, the light source system 110 may include one or more light-emitting diodes or other light sources. In some implementations, the light-conveying system 115 may include optical fibers. Some examples are described below. In this example, the light-conveying system 115 is capable of conveying light from the light source system 110 to a user's first ear and the user's second ear, via a first earbud 105a and a second earbud 105b. In some examples, at least a portion of the light source system 110 may be included in an earbud 105. However in alternative examples, the light-conveying system 115 may be capable of conveying light to the earbuds 105 from a light source system 110 that is located outside of the earbuds 105.

The image sensor system 120 may be capable of forming images based, at least in part, on light reflected from a user's ear, e.g., light reflected from the user's right ear and light reflected from the user's left ear. For example, one portion of the light-conveying system 115 may be capable of conveying light to a user's ear via one of the earbuds 105. The earbud 105 may be capable of capturing at least part of the reflected light, for example via one or more lenses, and of coupling the reflected light into a second portion of the light-conveying system 115. The second portion of the light-conveying system 115 may be capable of conveying the reflected, coupled light to the image sensor system 120. The image sensor system 120 may, for example, include one or more arrays of semiconductor charge-coupled devices (CCD), complementary metal-oxide-semiconductor (CMOS) devices or N-type metal-oxide-semiconductor (NMOS) devices. In some implementations, the earbuds 105 may include at least a portion of the image sensor system 120. However, in some implementations the light-conveying system 115 may be capable of conveying the light reflected from the user's first ear and the user's second ear from the earbuds 105 to at least a portion of the image sensor system 120 that is located separate from and/or in another part of the otoscope system 100.

According to some implementations, the image sensor system 120 may include and/or be a component of a sensor system that includes other types of sensors. In some such examples, the other sensors may include one or more temperature sensors. For example, some implementations may include a temperature sensor in at least one earbud of the earbuds 105. The temperature sensor may be capable of determining a user's body temperature. The temperature sensor may be capable of providing an indication of the temperature of a user's ear to the control system 125.

The control system 125 may include at least one of a general purpose single- or multi-chip processor, a digital signal processor (DSP), an application specific integrated circuit (ASIC), a field programmable gate array (FPGA) or other programmable logic device, discrete gate or transistor logic, or discrete hardware components. The control system 125 may be capable of performing some or all of the methods described herein. In some implementations, the control system 125 may be capable of controlling one or more components of the otoscope system 100. For example, in one implementation, the control system 125 is capable of controlling the light source system 110, the light conveying system 115 and the image sensor system 120.

In some implementations, the control system 125 may be capable of controlling the otoscope system 100 according to instructions (e.g., software) stored on non-transitory media. Such non-transitory media may include one or more memory devices of the otoscope system 100, which may include one or more random access memory (RAM) devices, one or more read-only memory (ROM) devices, etc. Accordingly, at least some aspects of the subject matter disclosed herein may be implemented via a non-transitory medium having software stored thereon.

In the example shown in FIG. 1, the otoscope system 100 includes an optional interface system 130. The interface system 130 includes a wireless interface system in this example. In some implementations, the interface system 130 may include a network interface, an interface between the control system 125 and a memory system and/or an external device interface (e.g., a port). In this implementation, the otoscope system 100 is capable of wireless communication with a second device via the interface system 130. Some examples are described below.

Figure 2:
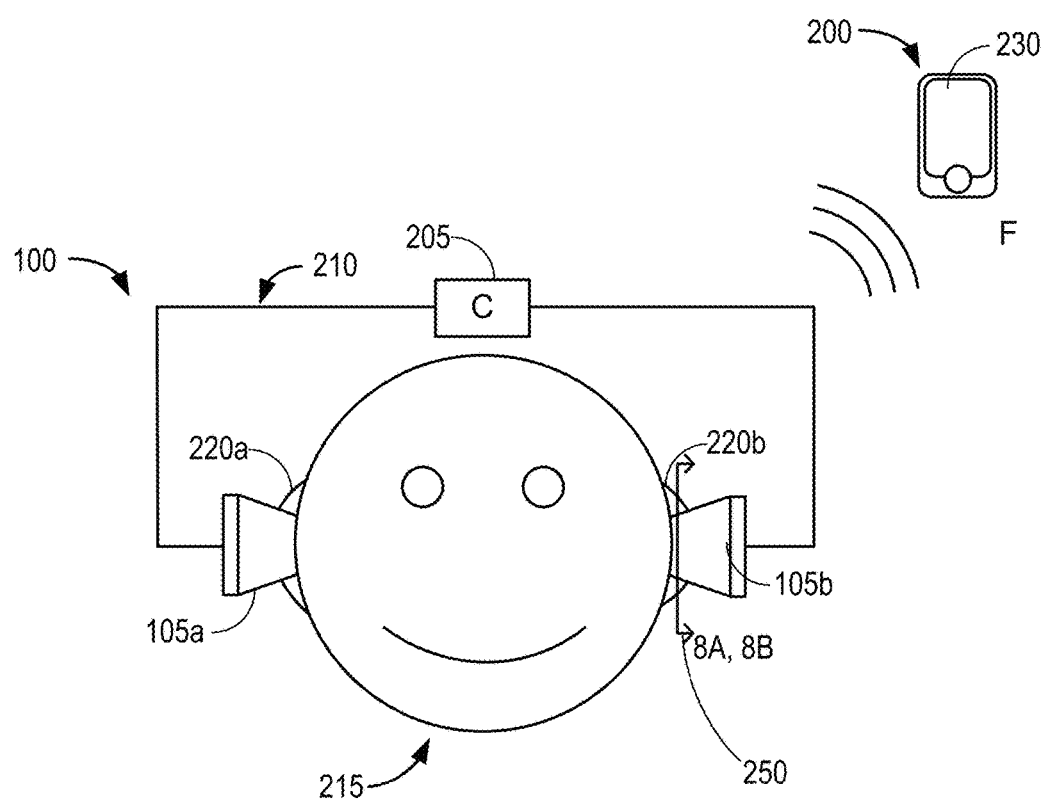
FIG. 2 shows examples of otoscope system elements according to some implementations.

FIG. 2 shows examples of elements of an otoscope system 100 according to some implementations. As with other implementations disclosed herein, the numbers of elements and types of elements shown in FIG. 2 are merely shown by way of example. Other implementations may have more, fewer or different elements. In this implementation, the otoscope system 100 includes a connecting element 210 that is capable of connecting the earbuds 105*a* and 105*b* with the unit 205. In some examples, the connecting element 210 may be a headband that is attachable to the earbuds 105*a* and 105*b* and that is capable of holding the earbud 105*a* in the user 215's ear 220*a* and of holding the earbud 105*a* in the user 215's ear 220*b*. Some such implementations may be capable of holding the earbuds 105*a* and 105*b* firmly in place and of aligning the earbuds 105*a* and 105*b* properly without the need for user adjustment.

The unit 205 may include the light source system 110, the image sensor system 120, the control system 125 and/or the interface system 130 that are shown in FIG. 1. However, one or more of these elements may be included in other components of the otoscope system 100, such as in one or both of the earbuds 105*a* and 105*b*. For example, in some implementations the unit 205 may include at least a portion of the light source system 110 The connecting element 210 may include at least a portion of the light-conveying system 115, such as optical fibers, capable of conveying light from a light source of the unit 205 to the earbuds 105*a* and 105*b*.

In some implementations, the unit 205 may include at least a portion of the image sensor system 120. According to some such implementations, a portion of the light-conveying system 115 included in, or attached to, the connecting element 210 may be capable of conveying light from the earbuds 105*a* and 105*b* to at least a portion of the image sensor system 120 included in the unit 205. In some such implementations, at least some optical fibers of the light-conveying system 115 may be disposed within the connecting element 210.

In this example, as shown for example in FIG. 1, the otoscope system 100 includes an interface system 130 (not shown in FIG. 2) that is capable of wireless communication with a second device, such as a wireless mobile device. According to some such implementations, the unit 205 may include at least a portion of the interface system 130. Alternatively, or additionally, the earbud 105*a*, the earbud 105*b*, or both of the earbuds 105*a* and 105*b* may include at least a portion of the interface system 130. In the example shown in FIG. 2, the otoscope system 100 is in communication with a smart phone 200 via the interface system 130.

According to some examples, the control system 125 may be capable of providing image data, via the interface system 130, to a second device. In this example, the control system 125 may be capable of providing image data, via the interface system 130, to the smart phone 200 that is shown in FIG. 2. If the second device includes a display, the second device may be capable of displaying images that correspond with the received image data. For example, the smart phone 200 may be capable of displaying images on the display system 230 of the ear 220*a*, the ear 220*b*, or both, corresponding to image data received from the otoscope system 100.

Figure 3:
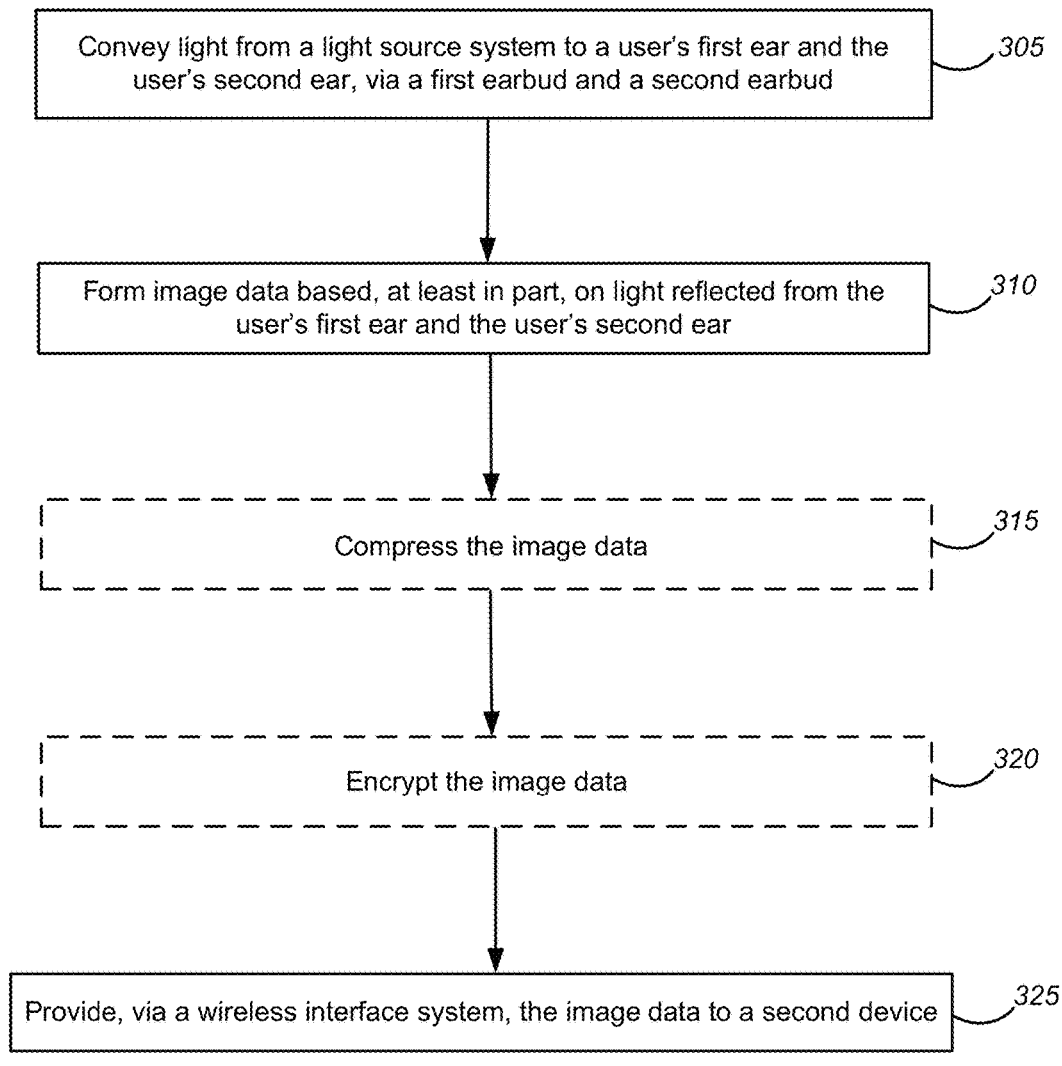
FIG. 3 is a block diagram that outlines one example of a method for controlling a wearable otoscope system.

FIG. 3 is a block diagram that outlines one example of a method for controlling a wearable otoscope system. The blocks of method 300, like other methods described herein, are not necessarily performed in the order indicated. Moreover, such methods may include more or fewer blocks than shown and/or described. In one example, the method may be implemented by the dual-ear otoscope 100 described in FIGS. 1 and 2. The blocks of method 300 may, for example, be performed by a control system such as the control system 125 that is shown in FIG. 1 and described above. Although the blocks of method 300 are described below with reference to FIGS. 1 and 2, method 300 also may be performed by alternative otoscope systems 100, such as the alternative implementations disclosed herein.

In this example, block 305 involves conveying light from a light source system to a user's first ear and the user's second ear, via a first earbud and a second earbud. According to some implementations described above with reference to FIGS. 1 and 2, block 305 may involve conveying light from a light source of the unit 205 to the ear 220a and the ear 220b via a light-conveying system 115. The light-conveying system 115 may include optical fibers within or on the connecting element 210. The light-conveying system 115 may include optical fibers within or on the earbuds 105a and 105b. In some examples, the light-conveying system 115 (or another part of the otoscope system 100) may include optical elements within or on the earbuds 105a and 105b, such as lenses, mirrors, micromechanical systems (MEMS) devices, etc., as described elsewhere herein.

In this implementation, block 310 involves forming image data based, at least in part, on light reflected from the user's first ear and the user's second ear. Block 310 may, for example, be performed by an image sensor system such as the image sensor system 120 disclosed herein. In some examples, block 310 may be performed by portions of an image sensor system 120 that is included in the earbuds 105a and 105b. In alternative examples, block 310 may be performed by portions of an image sensor system 120 that is included in another part of the otoscope system 100, such as the unit 205. In some implementations, block 310 may be performed by an image sensor system 120 that is included in another device, such as the smart phone 200 that is shown in FIG. 2. The interface system 130 may include apparatus for coupling light to a camera of another device. In some such examples, the otoscope system 100 may include a light-conveying system 115 that is capable of conveying light to another device via the interface system 130.

According to this example, optional block 315 involves compressing the image data. The image data that is provided by the otoscope system 100 may, in some examples, be video data. Transmitting uncompressed video data may require a high data rate. Likewise, storing uncompressed video data may require a significant amount of memory. Accordingly, in some implementations, the control system 125 may be capable of compressing image data prior to transmitting the image data to a second device. According to some such implementations, the control system 125 may be capable of compressing image data via a lossy compression algorithm, such as a Moving Picture Experts Group (MPEG) compression algorithm, (for example, according to the MPEG-4 standard). However, in alternative implementations the control system 125 may be capable of compressing image data via a different lossy compression method or via a lossless compression method.

In this example, optional block 320 involves encrypting the image data. Block 320 may, for example, be performed by a control system such as the control system 125 disclosed herein. According to some examples, the control system 125 may be capable of encrypting image data via symmetric-key cryptography. In some such examples, the control system 125 may be capable of encrypting image data via a block cipher cryptographic method, e.g., according to the Data Encryption Standard (DES) or the Advanced Encryption Standard (AES). In some implementations, the control system 125 may be capable of encrypting image data via a cryptographic hash function, such as one of the Secure Hash Algorithm (SHA) series of functions, e.g., the SHA-1, the SHA-2 or the SHA-3 algorithm. According to some examples, the control system 125 may be capable of encrypting image data via asymmetric-key cryptography methods, such as public-key cryptography methods.

According to this example, block 325 involves providing, via a wireless interface system, the image data to a second device. In the example shown in FIG. 2, block 325 may involve providing, via a wireless interface system (e.g. of the unit 205), the image data to the smart phone 200.

In some implementations, the control system 125 may be capable of receiving instructions from a second device, via the interface system 130, and of controlling the otoscope system 100 according to the instructions. According to some such examples, the instructions may be sent from a smart phone, such as the smart phone 200 that is shown in FIG. 2. The instructions may correspond with user input received by the smart phone 200, e.g., via a user interface of the smart phone 200. However, in some examples the instructions may originate from another device, which may or may not be in the vicinity of the otoscope system 100. Some examples are described below.

The smart phone 200 of FIG. 2 (or another device) may be capable of receiving user input that is based, at least in part, a user's responses to the displayed images. For example, a user may desire to adjust the illumination provided by the light-conveying system 115, the focus of a lens in the earbud 105a or the earbud 105b, the intensity of light provided by the light source system 110, etc., in response to the displayed images and may provide corresponding user input to the smart phone 200. The smart phone 200 may be capable of sending instructions to the otoscope system 100 that correspond with the user input, e.g., via a user interface of the smart phone 200. According to some implementations, the interface system 130 may include a user interface that is capable of receiving user input. Such implementations may be capable of receiving user instructions directly, without the need for receiving the instructions via a second device such as the smart phone 200.

The control system 125 may be capable of receiving the instructions, via the interface system 130, and of controlling the otoscope system 100 according to the instructions. For example, in some implementations the light-conveying system 115 may include optical elements that are capable of controlling illumination angles of light provided by the light-conveying system 115 (or by another part of the otoscope system 100). In some such implementations, the optical elements may include one or more mirrors, lenses, etc. According to some such implementations, the optical elements may include one or more micromechanical systems (MEMS) devices. In some examples, the control system 125 may be capable of controlling illumination angles of light provided by the optical elements by providing signals to the optical elements. The signals may correspond with instructions received via the interface system 130.

In some implementations, the instructions received by the control system 125 may include instructions for controlling the intensity of light provided by the light source system 110. The control system 125 may be capable of controlling the light source system 110 according to the instructions.

As noted above, the earbuds 105a and 105b may include deformable material. In some implementations, the deformable material may include actively deformable material, such as an electroactive polymer. According to some such implementations, the control system 125 may be capable of controlling deformation of the actively deformable material. For example, the control system 125 may be capable of controlling deformation of the actively deformable material in order to adjust the position of a portion of the light-conveying system 115 (or another optical element of the otoscope system 100) that is attached to an earbud 105, in response to instructions received from a second device via the interface system 130. In some examples, the control system 125 may be capable of controlling deformation of the actively deformable material in order to adjust the position of a portion of a light-coupling system, such as a lens, that is attached to an earbud 105, in response to instructions received from a second device via the interface system 130.

Figure 4:
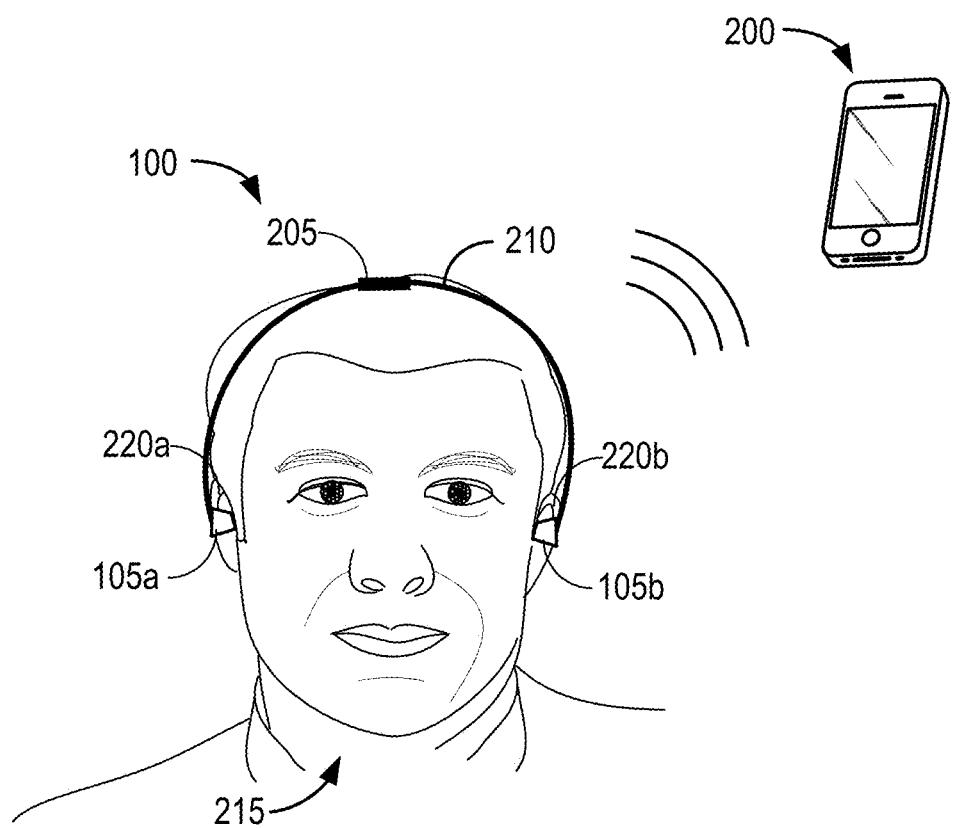
FIG. 4 shows examples of otoscope system elements according to some implementations.

FIG. 4 shows examples of otoscope system elements according to some implementations. As with other implementations disclosed herein, the numbers of elements and types of elements shown in FIG. 4 are merely shown by way of example. Other implementations may have more, fewer or different elements. In this implementation, the otoscope system 100 includes connecting element 210, a headband in this example, capable of connecting the earbuds 105*a* and 105*b* with the unit 205. In this example, the connecting element 210 is attachable to the earbuds 105*a* and 105*b* and is capable of holding the earbud 105*a* in the user 215's ear 220*a* and of holding the earbud 105*a* in the user 215's ear 220*b*. Some such implementations may be capable of holding the earbuds 105*a* and 105*b* firmly in place and/or aligning the earbuds 105*a* and 105*b* properly without the need for user adjustment.

In some implementations, the unit 205 may include at least a portion of the light source system 110. In this example, the unit 205 is attached to the connecting element 210. The connecting element 210 may include at least a portion of the light-conveying system 115, such as optical fibers, capable of conveying light from a light source of the light source system 110 to the earbuds 105*a* and 105*b*. In some implementations, the unit 205 may include at least a portion of the image sensor system 120 and the control system 125. According to some such implementations, a portion of the light-conveying system 115 included in, or attached to, the connecting element 210 may be capable of conveying light from the earbuds 105*a* and 105*b* to at least a portion of the image sensor system 120 included in the unit 205. In some such implementations, at least some optical fibers of the light-conveying system 115 may be disposed within or on the connecting element 210.

However, in some implementations at least a portion of the image sensor system 120 may be disposed in the earbud 105*a*, in the earbud 105*b*, or in both of the earbuds 105*a* and 105*b*. In some such examples, portions of the image sensor system 120 that are disposed in the earbuds 105*a* and 105*b* may be capable of providing image data to the control system 125, via wired or wireless communication. According to some such examples, portions of the image sensor system 120 that are disposed in the earbuds 105*a* and 105*b* may be capable of providing image data to the control system 125 via wires that are attached to, or included in, the connecting element 210.

In this implementation, the otoscope system 100 is capable of providing image data to a second device, which is the smart phone 200 in this example. In some implementations, the otoscope system 100 may be capable of receiving instructions from a second device, such as the smart phone 200, and of controlling the otoscope system 100 according to the instructions.

Figure 5:
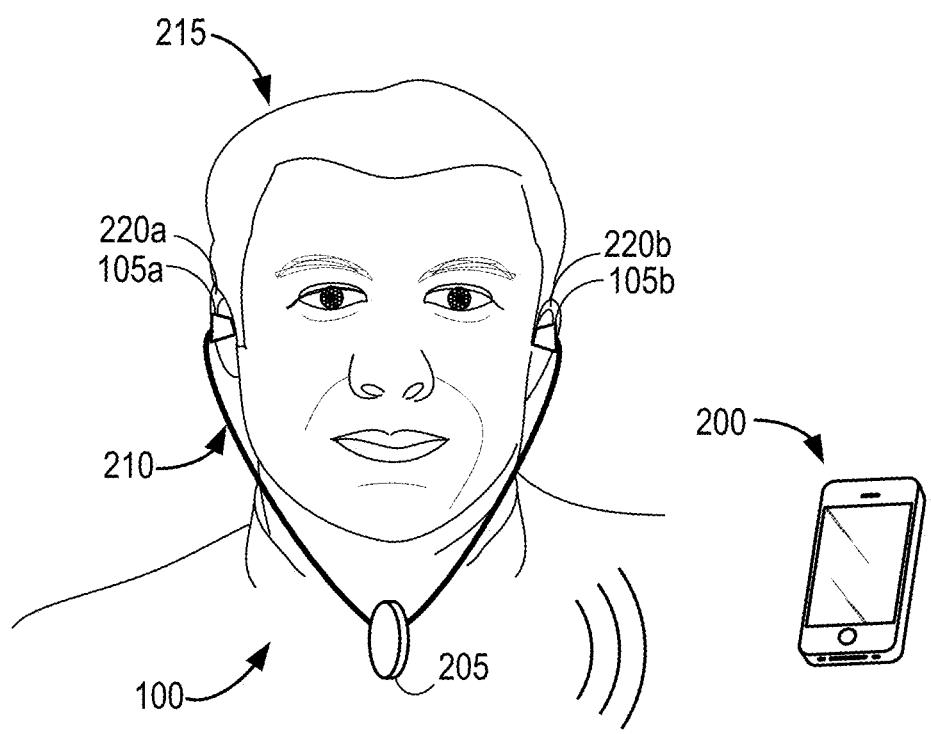
FIG. 5 shows alternative examples of otoscope system elements according to some implementations.

FIG. 5 shows alternative examples of otoscope system elements according to some implementations. As with other implementations disclosed herein, the numbers of elements and types of elements shown in FIG. 5 are merely shown by way of example. Other implementations may have more, fewer or different elements. In this implementation, the otoscope system 100 includes connecting element 210 that is capable of connecting the earbuds 105*a* and 105*b* with the unit 205. However, in this example the connecting element 210 is not intended to be worn as a headband. Instead, the unit 205 is intended to dangle from the connecting element 210. In some examples, as shown in FIG. 5, the otoscope system 100 may be designed such that the unit 205 is intended to dangle below the head of a user 215 when the otoscope system 100 is worn.

According to such examples, the connecting element 210 may or may not be capable of holding the earbud 105*a* in the user 215's ear 220*a* and of holding the earbud 105*a* in the user 215's ear 220*b*, depending on the particular implementation. In some implementations, the connecting element 210 may include a material with sufficient stiffness such that the connecting element 210 is capable of holding the earbuds 105*a* and 105*b* firmly in place and of aligning the earbuds 105*a* and 105*b* properly without the need for user adjustment. For example, the connecting element 210 may be formed of metal, a rigid plastic, etc. However, in alternative implementations, the connecting element 210 may not be formed of a rigid material.

In some implementations, the unit 205 may include at least a portion of the light source system 110. In this example, the unit 205 is attached to the connecting element 210. The connecting element 210 may include at least a portion of the light-conveying system 115, such as optical fibers, capable of conveying light from a light source of the light source system 110 to the earbuds 105*a* and 105*b*. In some implementations, the unit 205 may include at least a portion of the image sensor system 120 and the control system 125. According to some such implementations, a portion of the light-conveying system 115 included in, or attached to, the connecting element 210 may be capable of conveying light from the earbuds 105*a* and 105*b* to at least a portion of the image sensor system 120 included in the unit 205. In some such implementations, at least some optical fibers of the light-conveying system 115 may be disposed within or on the connecting element 210.

However, in some implementations at least a portion of the image sensor system 120 may be disposed in the earbud 105*a*, in the earbud 105*b*, or in both of the earbuds 105*a* and 105*b*. In some such examples, portions of the image sensor system 120 that are disposed in the earbuds 105*a* and 105*b* may be capable of providing image data to the control system 125, via wired or wireless communication. According to some such examples, portions of the image sensor system 120 that are disposed in the earbuds 105*a* and 105*b* may be capable of providing image data to the control system 125 via wires that are attached to, or included in, the connecting element 210.

In this implementation, the otoscope system 100 is capable of providing image data to a second device, which is the smart phone 200 in this example. According to the example shown in FIG. 5, the unit 205 includes an interface system 130 capable of providing wireless communication between the otoscope system 100 and a second device. In some implementations, the otoscope system 100 may be capable of receiving instructions from a second device, such as the smart phone 200, and of controlling the otoscope system 100 according to the instructions.

Figure 6:
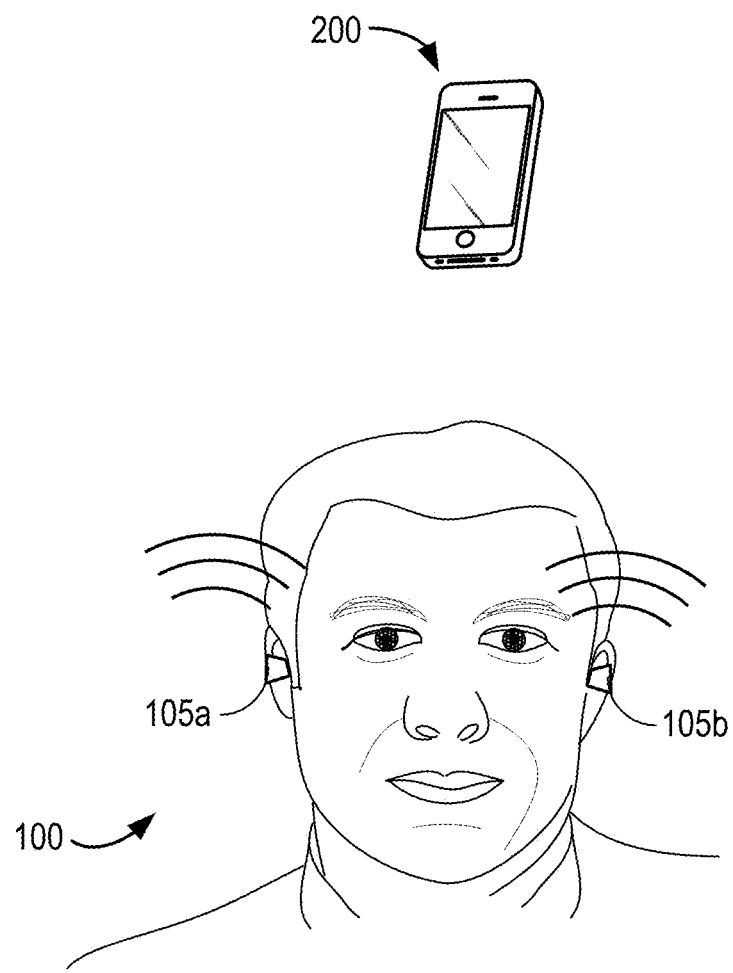
FIG. 6 shows alternative examples of otoscope system elements according to some implementations.

FIG. 6 shows alternative examples of otoscope system elements according to some implementations. As with other implementations disclosed herein, the numbers of elements and types of elements shown in FIG. 6 are merely shown by way of example. Other implementations may have more, fewer or different elements. In this implementation, the otoscope system 100 does not include a connecting element 210 for connecting the earbuds 105a and 105b. Moreover, in this example the otoscope system 100 does not include an element, separate from the earbuds 105a and 105b, which is comparable to the unit 205. Instead, in this example the earbuds 105a and 105b include all of the elements shown in FIG. 1: here, each of the earbuds 105a and 105b includes a light source system 110, a light-conveying system 115, an image sensor system 120, a control system 125 and an interface system 130.

Figure 7:
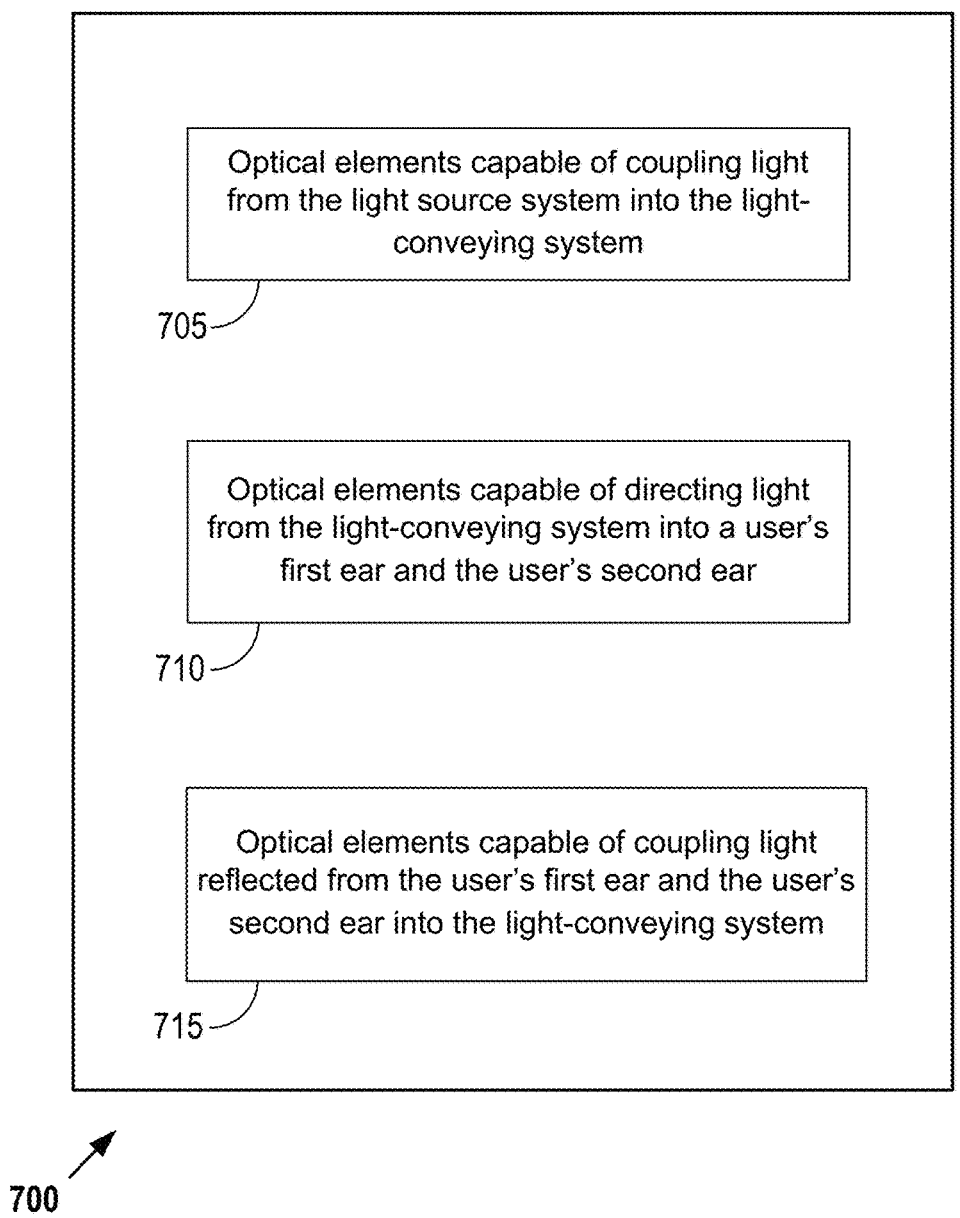
FIG. 7 is a block diagram that shows examples of optical elements according to some implementations.

FIG. 7 is a block diagram that shows examples of optical elements according to some implementations. As with other implementations disclosed herein, the numbers of elements and types of elements shown in FIG. 7 are merely shown by way of example. Other implementations may have more, fewer or different elements. In this implementation, the optical system 700 includes optical elements 705-715. According to this example, the optical elements 705 are capable of coupling light from the light source system into the light-conveying system 115. In this implementation, the optical elements 710 are capable of directing light from the light-conveying system 115 into a user's first ear and the user's second ear. In this example, the optical elements 715 are capable of coupling light reflected from the user's first ear and the user's second ear into the light-conveying system 115.

The optical elements 705-715 may, for example, include one or more mirrors, lenses, etc. According to some such implementations, the optical elements may include one or more MEMS devices. In some examples, the control system 125 may be capable of controlling illumination angles of light provided by the light-conveying system 115 by providing signals to the optical elements. The signals may correspond with instructions received from a second device via the interface system 130.

Figure 8A:
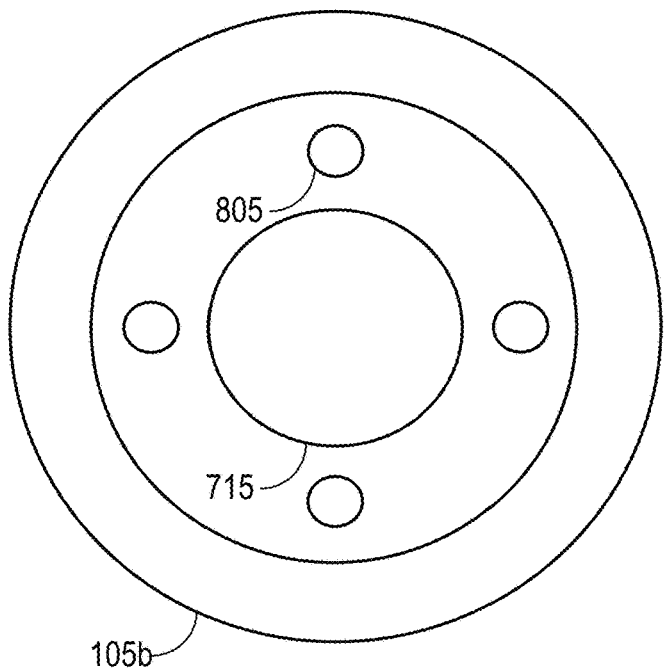
FIGS. 8A and 8B are examples of cross-sections through an earbud of an otoscope system according to some implementations.
Figure 8B:
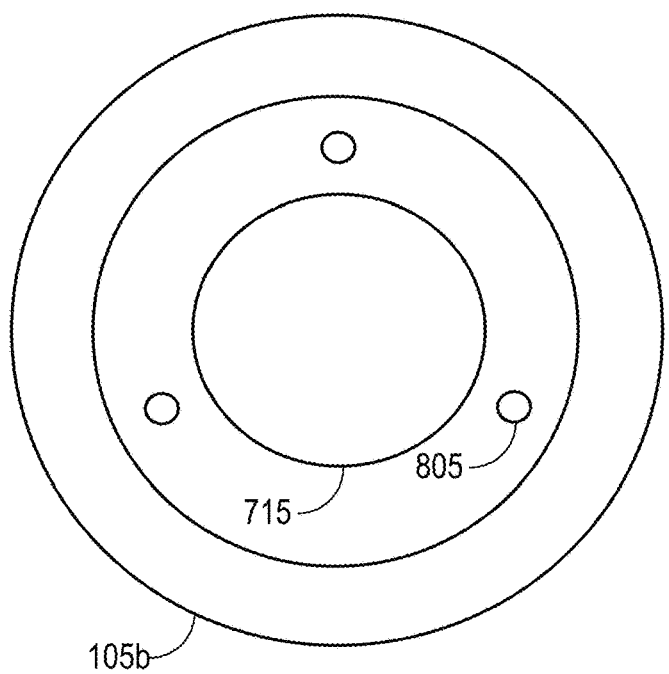

FIGS. 8A and 8B are examples of cross-sections through an earbud of an otoscope system according to some implementations. As with other implementations disclosed herein, the numbers of elements and types of elements shown in FIGS. 8A and 8B are merely shown by way of example. Other implementations may have more, fewer or different elements. In this example, FIGS. 8A and 8B are cross-sections taken through the cross-section line 250 that is shown in FIG. 2. Accordingly, FIGS. 8A and 8B are cross-sections taken through the earbud 105b in this example.

In the implementations shown in FIGS. 8A and 8B, the earbud 105b includes an optical element 715 in a central portion of the earbud 105b. The optical element 715 may, for example, be a lens or a lens system that is capable of coupling light reflected from a user's ear into a portion of a light-conveying system 115. Other examples may include additional optical elements 715, an optical elements 715 positioned in a different area of the earbud 105b, or both.

According to the example shown in FIG. 8A, the earbud 105b includes four optical fiber bundles 805 surrounding the optical element 715, whereas in the example shown in FIG. 8B, the earbud 105b includes three optical fiber bundles 805 surrounding the optical element 715. In both examples, the optical fiber bundles 805 are part of a light-conveying system 115 that is capable of conveying light from a light source system 110. In both examples, the optical fiber bundles 805 are capable of conveying light to one or more instances of optical elements 710, which is (or are) capable of directing light from the light-conveying system 115 into a user's ear. The optical element(s) 710 may include one or more lenses, mirrors, MEMS devices, etc. The optical element 710 may be positioned near a tip area of the earbud 105.

Figure 9A:
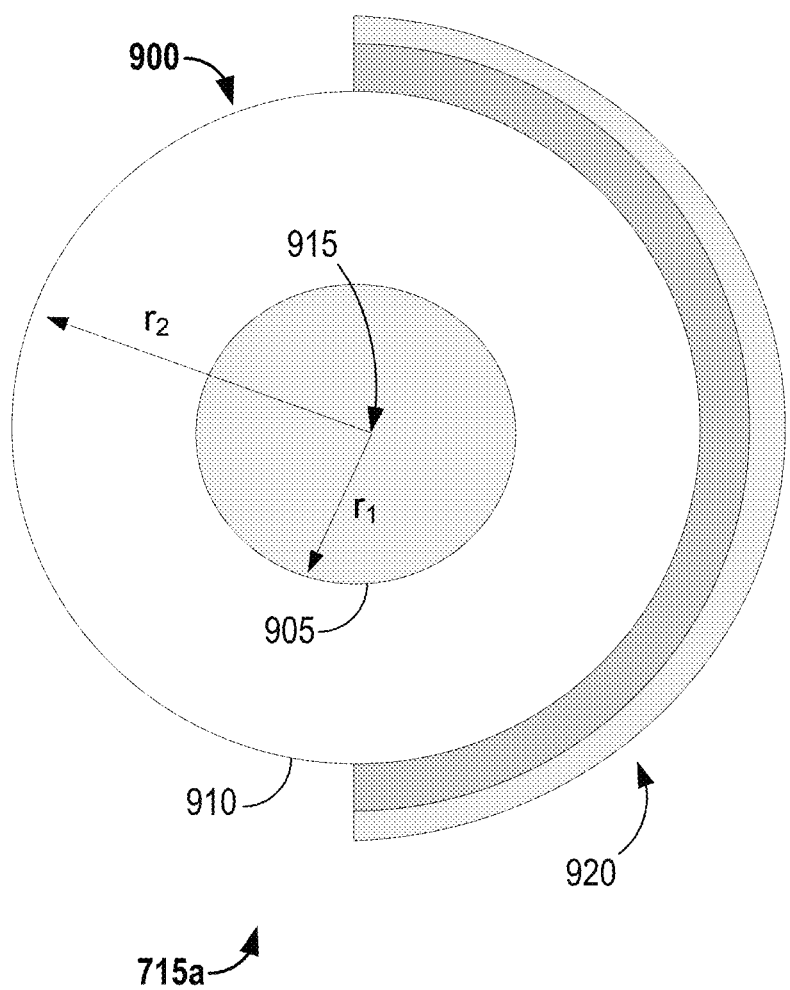
FIGS. 9A and 9B show examples of optical elements that are capable of coupling light reflected from a user's ear into a portion of a light-conveying system.
Figure 9B:
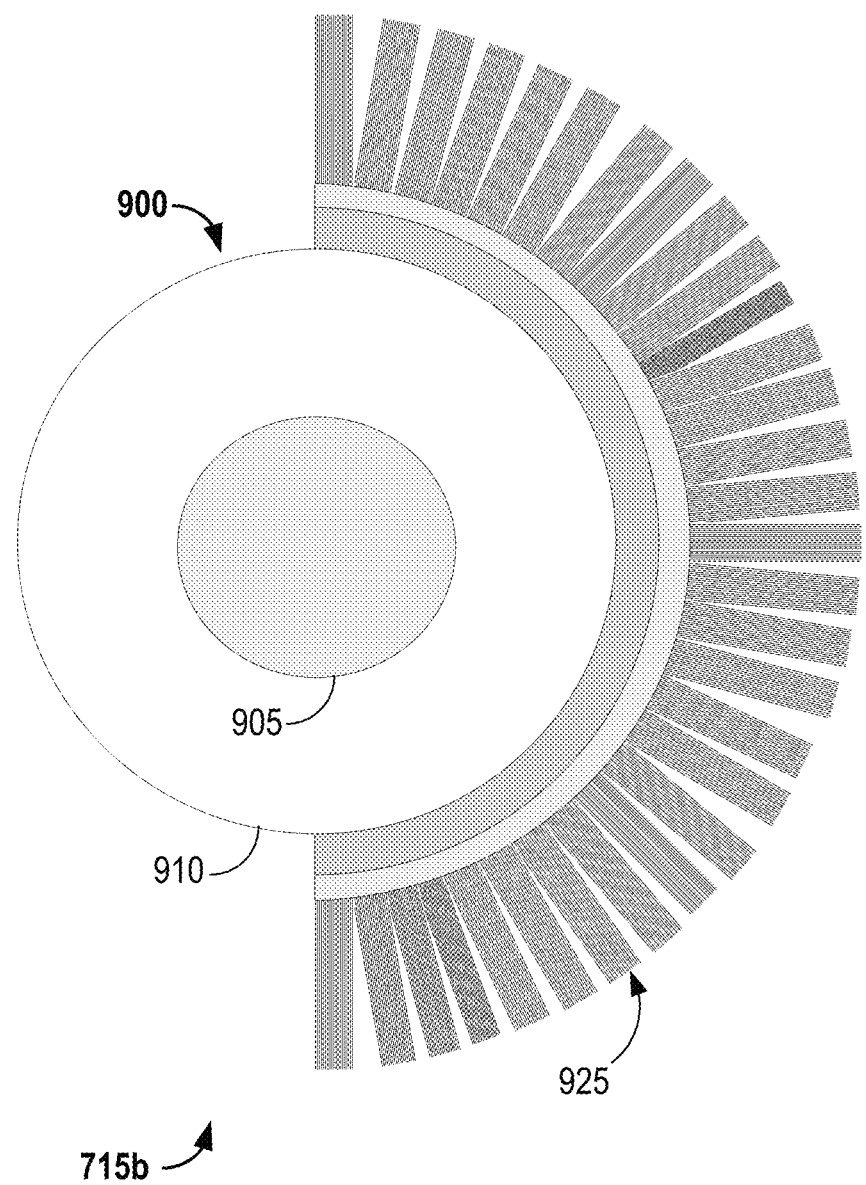

FIGS. 9A and 9B show examples of optical elements that are capable of coupling light reflected from a user's ear into a portion of a light-conveying system. As with other implementations disclosed herein, the numbers of elements and types of elements shown in FIGS. 9A and 9B are merely shown by way of example. Other implementations may have more, fewer or different elements. In this example, the optical element 715a shown in FIG. 9A and the optical element 715b shown in FIG. 9B both include a monocentric lens 900, which has spherical optical surfaces that share a single center of curvature. In these examples, the monocentric lenses 900 are "two-glass" monocentric lenses, including an inner portion 905 having a radius $r_1$ and an outer portion 910 having a radius $r_2$ from the same center 915. However, such monocentric lenses 900 are not necessarily formed of glass, but may instead be formed of any appropriate transparent or substantially transparent material, such as plastic. According to some examples, radius $r_1$ may be in the range of 3.73 mm to 3.78 mm and radius $r_2$ may be in the range of 7.58 mm to 9.05 mm. The inner portion 905 and the outer portion 910 may have different indices of refraction. For example, in some implementations the inner portion 905 may have an index of refraction in the range of 1.81 to 1.85 and the outer portion 910 may have an index of refraction in the range of 1.95 to 2.03.

Some implementations of the monocentric lens 900 may include a physical aperture stop or "iris," which may be within the monocentric lens. In some such implementations, a physical aperture stop may be provided by fabricating inner portion 905 as two hemispherical elements. However, other implementations of the monocentric lens 900 may include a virtual aperture stop, which may be achieved by limiting light transmission in the image transfer optics.

In the implementation shown in FIG. 9A, the optical element 715a includes image sensor system 920, which is a portion of the image sensor system 120 of an otoscope system 100. The image sensor system 920 may, for example, include one or more arrays of semiconductor charge-coupled devices (CCD), complementary metal-oxide-semiconductor (CMOS) devices or N-type metal-oxide-semiconductor (NMOS) devices. The image sensor system 920 may be capable of providing image data to a control system 125 of the otoscope system 100.

In the implementation shown in FIG. 9B, the optical element 715b does not include an image sensor system. Instead, the optical element 715b includes a plurality of optical fiber bundles 925, which are portions of the light-conveying system 115 of an otoscope system 100. The optical fiber bundles 925 may be straight or tapered optical fiber bundles, depending on the particular implementation. Some implementations of the optical element 715b that include a monocentric lens 900 having a physical aperture stop may, for example, include straight optical fiber bundles whereas some implementations of the optical element 715b that include a monocentric lens 900 having a virtual aperture stop may include tapered optical fiber bundles.

In some examples, the optical fiber bundles 925 may be capable of providing light reflected from an ear to an image sensor system 120 that is disposed in another element of the otoscope system 100. In alternative examples, the optical fiber bundles 925 may be capable of providing light reflected from an ear to an image sensor system 120 that is disposed in a local portion of an image sensor system 120 that is disposed in an earbud.

Figure 10:
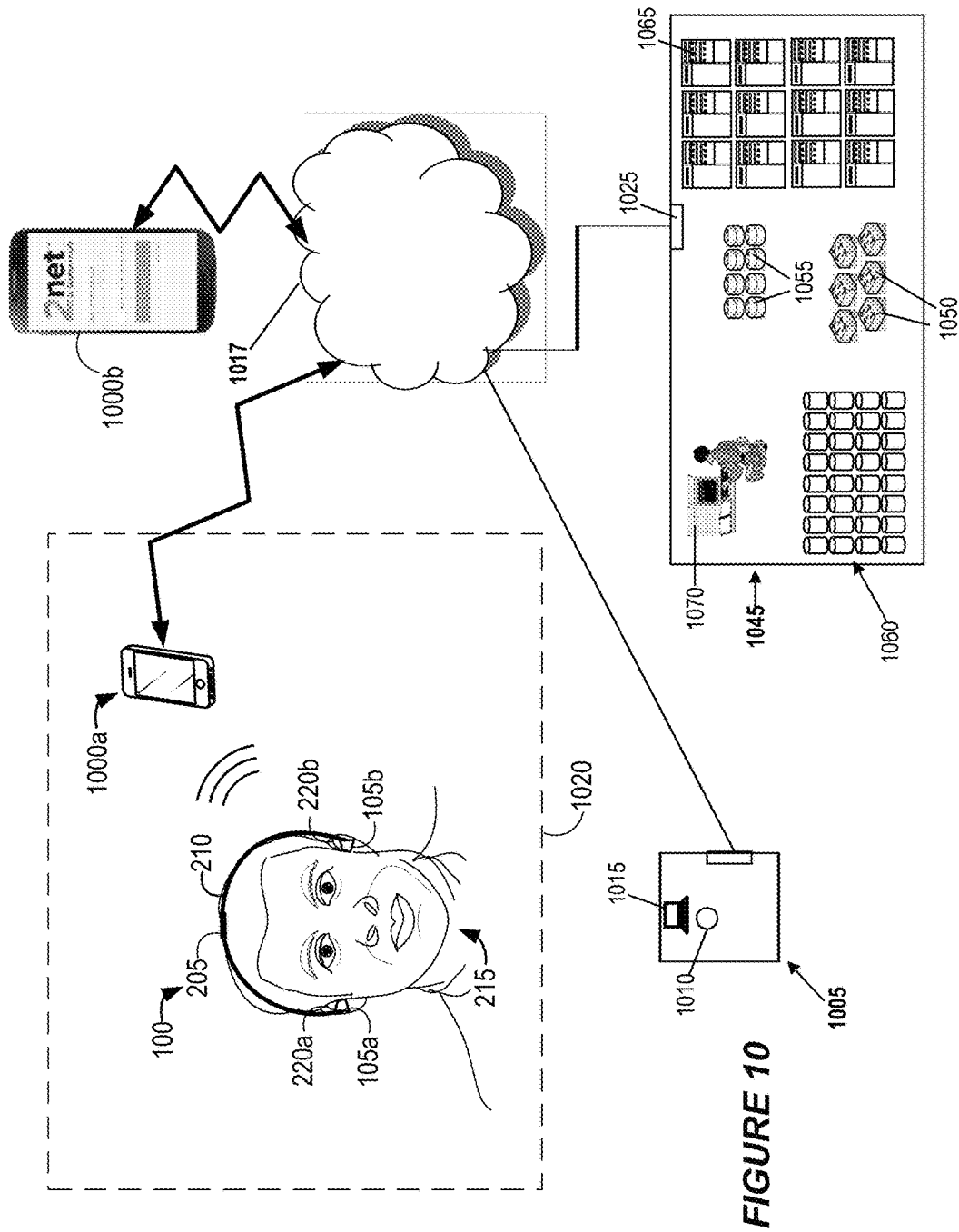
FIG. 10 is a block diagram that shows examples of components of a system in which some aspects of the present disclosure may be implemented.

FIG. 10 is a block diagram that shows examples of components of a system in which some aspects of the present disclosure may be implemented. The numbers, types and arrangements of devices shown in FIG. 10 are merely shown by way of example. In this example, various devices are capable of communication via one or more networks 1017. The networks 1017 may, for example, include the public switched telephone network (PSTN), including cellular telephone networks, the Internet, etc. The mobile devices 1000a and 1000b shown in FIG. 10 may, for example, include personal computing devices such as smart phones, cellular telephones, tablet devices, etc.

At location 1020, a mobile device 1000a is capable of wireless communication with the otoscope system 100. The mobile device 1000a is one example of a "second device" referenced in the foregoing discussion. The mobile device 1000a may, for example, be capable of executing software to perform some of the methods described herein, such as receiving image data, decrypting image data, displaying images corresponding with received image data, receiving user input and sending control signals to the otoscope system 100, etc.

In this example, a data center 1045 includes various devices that may be capable of providing health information services via the networks 1017. Accordingly, the data center 1045 is capable of communication with the networks 1017 via the gateway 1025. Switches 1050 and routers 1055 may be capable of providing network connectivity for devices of the data center 1045, including storage devices 1060, servers 1065 and workstations 1070. Although only one data center 1045 is shown in FIG. 10, some implementations may include multiple data centers 1045.

One or more types of devices in the data center 1045 (or elsewhere) may be capable of executing middleware, e.g., for data management and/or device communication. Health-related information, including but not limited to information obtained by networked otoscope systems 100, may be uploaded (e.g., from mobile devices such as mobile device 1000a) and stored on storage devices 1060 and/or servers 1065. Health-related software also may be stored on storage devices 1060 and/or servers 1065. In some implementations, some such health-related software may be available as "apps" and downloadable by authorized users. Some such apps may be executable on devices that are capable of communication with otoscope systems 100, such as the mobile device 1000a.

In this example, various people and/or entities, including but not limited to health care professionals, patients, patients' families, insurance company representatives, etc., may obtain information regarding, or obtained by, otoscope systems 100. The information may include, but may not be limited to, image data obtained by one or more otoscope systems 100, other sensor data (such as temperature data) obtained by one or more otoscope systems 100, etc.

In some examples, authorized people and/or entities may obtain such information via the data center 1045. Alternatively, at least some people and/or entities may be authorized to obtain such information via a data feed from otoscope systems 100, e.g., via corresponding devices that are in communication with the otoscope systems 100. Accordingly, in some examples one or more other devices (such as mobile devices 1000 or devices of the data center 1045) may act as intermediaries for such data feeds. Such devices may, for example, be capable of applying data encoding algorithms, data compression algorithms, data encryption algorithms, data filtering algorithms, executing data summary and/or analysis software, etc. In some implementations, data encoding algorithms, data decoding algorithms, data compression algorithms, data encryption and decryption algorithms, data filtering, summary software, analysis software, etc., may be available as "apps" and downloadable (e.g., from the data center 1045) by authorized users.

In this example, a family member of an authorized user is logging into the system, via the mobile device 1000b, in order to access physiological data obtained by the otoscope system 100 from the user 215 in location 1020. FIG. 10 also depicts a doctor's office 1005, from which a health care professional 1010 is using a laptop 1015 to access information from the data center 1045. The information may include information obtained by the otoscope system 100, or by other the otoscope systems 100.

Some implementations disclosed herein may be capable of providing authentication and/or identification functionality. For example, one of the servers 1065 of the data center 1045 may be capable of controlling access to information obtained by networked otoscope systems 100. In some such examples, a server 1065 may provide access to such information only after a user has provided an authentic user name and a corresponding password, e.g., via the mobile device 1000b or the laptop 1015, which have been accepted by the server 1065. The user name and password may have been established during a prior enrollment process.

According to some implementations, one or more of the devices shown in FIG. 10 may be capable of obtaining biometric information. For example, in some implementations the mobile device 1000a, the mobile device 1000b and/or the laptop 1015 may include a biometric sensor system, which may include a fingerprint sensor system, a camera system, etc. In some examples, a server 1065 may provide access to information obtained by networked otoscope systems 100 only after a user has provided fingerprint information or other biometric information (e.g., via the mobile device 1000a, the mobile device 1000b or the laptop 1015) that has been authenticated by the server 1065. (As used herein, "fingerprint information" includes print information corresponding to any digit, including fingerprint images and thumbprint images.) The server 1065 may, for example, compare the provided fingerprint or other biometric information (also referred to herein as "currently-obtained biometric information") with stored biometric information that was obtained during a prior enrollment process (also referred to herein as "previously-obtained biometric information").

In alternative implementations, another device may be capable of providing authentication and/or identification functionality. For example, in some implementations, a control system 125 of an otoscope system 100, a control system of a mobile device, or both, may include authentication and/or identification functionality.

In some implementations, biometric information may be used to verify the identity of a user of an otoscope system 100, the identity of a user of an associated mobile device, or both. For example, referring to FIG. 10, in some instances the user 215 may be controlling the mobile device 1000a while the otoscope system 100 is obtaining image data from ears of the user 215. However, in other instances another person, such as a doctor, a nurse, a pharmacy employee, a parent, or another care provider may be using the mobile device 1000a while the otoscope system 100 is obtaining image data from ears of the user 215.

In some examples, a biometric sensor system of the mobile device 1000a, such as a fingerprint sensor system, may obtain biometric information from a user. Alternatively, or additionally, in some examples a biometric sensor system of the otoscope system 100 may obtain biometric information from a user. Some examples are described below. A control system may perform an authentication process that is based, at least in part, on the biometric information in order to verify the identity of the user. For example, the authentication process may involve comparing currently-obtained biometric information with previously-obtained biometric information from an authorized user. Depending on the particular implementation, the control system may reside in the mobile device 1000a, in the otoscope system 100 or in another device (such as a server 1065).

If the authentication process is successful, in some implementations the control system may authorize a user whose identity has been verified to control the otoscope system 100 via the mobile device 1000a and/or to receive information from the otoscope system 100 via the mobile device 1000a. In some implementations, the image data and/or other sensor data that are acquired by the otoscope system 100 may be associated with identity information of the user. For example, the image data and/or other sensor data that are acquired by the otoscope system 100 may be stored in a data structure that also includes the identity information of the user. In some examples, the identity information may include the user's name. In some instances, the identity information may include at least some of the biometric information that was obtained during the authentication process, such as fingerprint information.

As noted above, in some examples, the otoscope system 100 may be capable of obtaining biometric information from a user. The shape of the outer ear, including the folds of the pinna and the length and shape of the ear canal, can vary significantly from person to person. Therefore, according to some such examples, the biometric information obtained by the otoscope system 100 may include image data obtained from one or more of the user's ears.

In another example, the structural differences between human ears also may be determined by acoustical measurements. There is evidence in the relevant scientific literature indicating that structural differences between human ears that are determined by acoustical measurements may be even more pronounced than structural differences between human ears that are determined according to image data.

Therefore, according to some such examples, the biometric information obtained by the otoscope system 100 may include information that corresponds to the acoustical properties of one or more of the user's ears. According to some such examples, the biometric information may include information corresponding to a "transfer function" of one or more of the user's ear canals. One or more features of the transfer function (such as amplitude information, phase information, delay information, etc.) may be evaluated in order to compare currently-obtained biometric information with previously-obtained biometric information.

In some such implementations, at least one earbud 105 of the otoscope system 100 may include a speaker and a microphone. The control system 125 may be capable of controlling the speaker to generate input acoustic signals while controlling the microphone to obtain output acoustic signals corresponding to the reflections of the input acoustic signals from a user's ear canal.

The control system 125 may be capable of determining a transfer function based, at least in part, on the input acoustic signals and the output acoustic signals. According to some implementations, part of the process of determining the transfer function may involve converting the input acoustic signals and the output acoustic signals from the time domain to the frequency domain. According to some such implementations, the control system 125 may be capable of determining the transfer function by performing operations on the input acoustic signals and the output acoustic signals in the frequency domain. In some examples, the control system 125 may be capable of determining the transfer function by dividing the frequency-domain output acoustic signals by the frequency-domain input acoustic signals.

However, in other implementations the control system 125 may be capable of determining the transfer function by applying an adaptive filter to minimize an error signal. The error signal may, for example, correspond with a difference between the output acoustic signals and an estimate of the transfer function that is based, in part, on the input acoustic signals.

As used herein, a phrase referring to "at least one of" a list of items refers to any combination of those items, including single members. As an example, "at least one of: a, b, or c" is intended to cover: a, b, c, a-b, a-c, b-c, and a-b-c.

The various illustrative logics, logical blocks, modules, circuits and algorithm processes described in connection with the implementations disclosed herein may be implemented as electronic hardware, computer software, or combinations of both. The interchangeability of hardware and software has been described generally, in terms of functionality, and illustrated in the various illustrative components, blocks, modules, circuits and processes described above. Whether such functionality is implemented in hardware or software depends upon the particular application and design constraints imposed on the overall system.

The hardware and data processing apparatus used to implement the various illustrative logics, logical blocks, modules and circuits described in connection with the aspects disclosed herein may be implemented or performed with a general purpose single- or multi-chip processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, e.g., a combination of a DSP and a microprocessor, a plurality of microprocessors, one or more microprocessors in conjunction with a DSP core, or any other such configuration. In some implementations, particular processes and methods may be performed by circuitry that is specific to a given function.

In one or more aspects, the functions described may be implemented in hardware, digital electronic circuitry, computer software, firmware, including the structures disclosed in this specification and their structural equivalents thereof, or in any combination thereof. Implementations of the subject matter described in this specification also may be implemented as one or more computer programs, i.e., one or more modules of computer program instructions, encoded on a computer storage media for execution by, or to control the operation of, data processing apparatus.

If implemented in software, the functions may be stored on or transmitted over as one or more instructions or code on a computer-readable medium, such as a non-transitory medium. The processes of a method or algorithm disclosed herein may be implemented in a processor-executable software module which may reside on a computer-readable medium. Computer-readable media include both computer storage media and communication media including any medium that may be enabled to transfer a computer program from one place to another. Storage media may be any available media that may be accessed by a computer. By way of example, and not limitation, non-transitory media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection may be properly termed a computer-readable medium. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and instructions on a machine readable medium and computer-readable medium, which may be incorporated into a computer program product.

Various modifications to the implementations described in this disclosure may be readily apparent to those having ordinary skill in the art, and the generic principles defined herein may be applied to other implementations without departing from the spirit or scope of this disclosure. Thus, the disclosure is not intended to be limited to the implementations shown herein, but is to be accorded the widest scope consistent with the claims, the principles and the novel features disclosed herein. The word "exemplary" is used exclusively herein, if at all, to mean "serving as an example, instance, or illustration." Any implementation described herein as "exemplary" is not necessarily to be construed as preferred or advantageous over other implementations.

Certain features that are described in this specification in the context of separate implementations also may be implemented in combination in a single implementation. Conversely, various features that are described in the context of a single implementation also may be implemented in multiple implementations separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products. Additionally, other implementations are within the scope of the following claims. In some cases, the actions recited in the claims may be performed in a different order and still achieve desirable results.

It will be understood that unless features in any of the particular described implementations are expressly identified as incompatible with one another or the surrounding context implies that they are mutually exclusive and not readily combinable in a complementary and/or supportive sense, the totality of this disclosure contemplates and envisions that specific features of those complementary implementations may be selectively combined to provide one or more comprehensive, but slightly different, technical solutions. It will therefore be further appreciated that the above description has been given by way of example only and that modifications in detail may be made within the scope of this disclosure.

What is claimed is:

1. An apparatus, comprising:
   a first earbud;
   a second earbud;
   a light source system that includes at least one light source;
   a light-conveying system capable of conveying light from the light source system to a user's first ear and to the user's second ear, via the first earbud and the second earbud;
   an image sensor system capable of forming images based, at least in part, on light reflected from the user's first ear and the user's second ear;
   wherein the first earbud and the second earbud include an actively deformable material; and
   a control system capable of controlling the light source system, controlling deformation of the actively deformable material, and controlling the image sensor system.

2. The apparatus of claim 1, further comprising an interface system capable of wireless communication with a second device.

3. The apparatus of claim 2, wherein the control system is capable of:
   receiving instructions from the second device, via the interface system; and
   controlling the apparatus according to the instructions.

4. The apparatus of claim 2, wherein the control system is capable of providing image data to the second device.

5. The apparatus of claim 4, wherein the control system is capable of compressing the image data prior to transmitting the image data to the second device.

6. The apparatus of claim 4, wherein the control system is capable of encrypting the image data prior to transmitting the image data to the second device.

7. The apparatus of claim 1, wherein the light-conveying system includes optical fibers.

8. The apparatus of claim 1, wherein the light-conveying system is capable of conveying the light reflected from the user's first ear and the user's second ear to the image sensor system.

9. The apparatus of claim 1, further comprising:
   first optical elements capable of coupling light from the light source system into the light-conveying system;
   second optical elements capable of directing light from the light-conveying system into the user's first ear and the user's second ear; and
   third optical elements capable of coupling light reflected from the user's first ear and the user's second ear into the light-conveying system.

10. The apparatus of claim 9, wherein the control system is capable of controlling illumination angles of light provided by the second optical elements.

11. The apparatus of claim 9, wherein the second optical elements include micromechanical systems (MEMS) devices.

12. The apparatus of claim 1, further comprising a headband attachable to the first earbud and the second earbud, the headband capable of holding the first earbud in a user's first ear and of holding the second earbud in the user's second ear.

13. The apparatus of claim 12, wherein at least a portion of the light-conveying system is attached to the headband.

14. The apparatus of claim 1, wherein the first earbud or the second earbud includes at least a portion of the image sensor system.

15. The apparatus of claim 1, wherein at least a portion of the control system is disposed within the first earbud or the second earbud.

16. The apparatus of claim 1, wherein the actively deformable material includes an electroactive polymer.

17. The apparatus of claim 1, further comprising a temperature sensor capable of measuring the user's body temperature.

18. The apparatus of claim 1, further comprising a biometric sensor system capable of obtaining biometric information from the user.

19. The apparatus of claim 18, wherein the biometric sensor system includes a speaker and a microphone.

20. The apparatus of claim 19, wherein the control system is capable of controlling the speaker to generate input acoustic signals while controlling the microphone to obtain output acoustic signals corresponding to the reflections of the input acoustic signals from a user's ear canal.

21. The apparatus of claim 20, wherein the control system is capable of determining a transfer function based, at least in part, on the input acoustic signals and the output acoustic signals.

22. An apparatus, comprising:
a first earbud;
a second earbud;
wherein the first earbud and the second earbud include an actively deformable material;
light source means for providing light;
light-conveying means for conveying light from the light source means to a user's first ear and the user's second ear, via the first earbud and the second earbud;
image sensor means for forming images based, at least in part, on light reflected from the user's first ear and the user's second ear; and
control means for controlling the light source means, controlling the means for actively deforming material, and the image sensor means.

23. The apparatus of claim 22, further comprising interface means for wireless communication with a second device.

24. The apparatus of claim 23, wherein the control means includes means for:
receiving instructions from the second device, via the interface means; and
controlling the apparatus according to the instructions.

* * * * *